(12) United States Patent
Tipler et al.

(10) Patent No.: US 7,552,618 B2
(45) Date of Patent: *Jun. 30, 2009

(54) CHROMATOGRAPHIC INTERFACE FOR THERMAL DESORPTION SYSTEMS

(75) Inventors: Andrew Tipler, Trumbull, CT (US); Heidi Grecsek, Shelton, CT (US); Frank DeLorenzo, Stratford, CT (US); Giuseppe Coppola, West Haven, CT (US)

(73) Assignee: PerkinElmer LAS, Inc., boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/876,378

(22) Filed: Oct. 22, 2007

(65) Prior Publication Data

US 2008/0041137 A1   Feb. 21, 2008

Related U.S. Application Data

(63) Continuation of application No. 11/169,935, filed on Jun. 29, 2005, now Pat. No. 7,284,410.

(60) Provisional application No. 60/521,749, filed on Jun. 29, 2004.

(51) Int. Cl.
*G01N 30/04* (2006.01)

(52) U.S. Cl. ............... 73/23.42; 73/23.35; 95/82; 96/101; 96/105; 96/106

(58) Field of Classification Search ............... 73/23.35, 73/23.41, 23.42; 95/82; 96/101, 105, 106; 422/89

See application file for complete search history.

(56) References Cited

U.S. PATENT DOCUMENTS

| 3,672,226 | A | * | 6/1972 | Reid | 73/864.86 |
| 5,545,252 | A | | 8/1996 | Hinshaw et al. | 95/15 |
| 6,402,947 | B1 | | 6/2002 | Altamirano et al. | 210/198 |
| 6,652,625 | B1 | | 11/2003 | Tipler et al. | 95/82 |
| 6,814,785 | B2 | | 11/2004 | Tipler et al. | 96/105 |
| 7,284,410 | B2 | * | 10/2007 | Tipler et al. | 73/23.42 |
| 2002/0157453 | A1 | | 10/2002 | Van der Maas | 73/23.35 |

FOREIGN PATENT DOCUMENTS

DE   43 16 375   6/1994
WO   WO 2005/040786   5/2005

OTHER PUBLICATIONS

International Search Report, Oct. 15, 2005, 7 pages.

* cited by examiner

*Primary Examiner*—Daniel S Larkin
(74) *Attorney, Agent, or Firm*—St. Onge Steward Johnston & Reens LLC

(57) ABSTRACT

Disclosed are systems and methods that include a thermal desorption unit, a chromatographic column, and an interface device between the unit and the column. The interface device controls the fluid flowing into the column, such as by providing additional carrier gas to maintain a substantially constant gas flow or velocity, by proving a controlled temperature increase, or by venting a portion of the gas received from the thermal desorption unit, thereby removing the dependence on the thermal desorption unit for such control. In some embodiments, the interface is a chromatographic injector. In certain embodiments, a transfer line from the desorption unit is coupled to the same port of the interface device as the chromatographic column. In some of these embodiments, this is accomplished by employing a special adaptor.

20 Claims, 6 Drawing Sheets

CHROMATOGRAPHIC INTERFACE FOR THERMAL DESORPTION SYSTEMS

RELATED APPLICATIONS

This application is a continuation of U.S. patent application Ser. No. 11/169,935 filed Jun. 29, 2005, now U.S. Pat. No. 7,284,410, which in turn claims priority benefits under 35 U.S.C. §119(e) of U.S. Provisional Patent Application Ser. No. 60/521,749 filed Jun. 29, 2004, the contents of which are herein incorporated by reference in their entirety.

FIELD OF THE INVENTION

The present invention relates to systems and methods for communicating analytes from a thermal desorption unit to a chromatographic column. More specifically, the invention relates to systems and methods relating to the use of an interface device to control the fluid flowing into the column.

BACKGROUND OF THE INVENTION

Gas chromatography is essentially a physical method of separation in which constituents of a vapor sample in a carrier gas are adsorbed or absorbed and then desorbed by a stationary phase material in a column. A pulse of the sample is introduced into a steady flow of carrier gas, which carries the sample into a chromatographic column. The inside of the column is lined with a liquid, and interactions between this liquid and the various components of the sample—which differ based upon differences among partition coefficients of the elements—cause the sample to be separated into the respective elements. At the end of the column, the individual components are more or less separated in time. Detection of the gas provides a time-scaled pattern, typically called a chromatogram, that, by calibration or comparison with known samples, indicates the constituents, and the specific concentrations thereof, which are present in the test sample. An example of the process by which this occurs is described in U.S. Pat. No. 5,545,252 to Hinshaw.

One common application of chromatographic analysis is the use of thermal desorption units to determine the constituents of a particular environment. For example, it is often desired to detect the amount of volatile organic compounds (VOCs) present in a certain sample of air. One way of doing this is by first transporting a tube packed with an adsorbent material into the environment to be tested, and allowing the VOCs in the air to migrate into the tube through natural diffusion, typically termed "diffusive" or "passive sampling." Alternatively, the VOCs may be collected by drawing a sample of gas (typically ambient air) through such a tube using a small vacuum pump, commonly referred to as "pumped sampling." In each case, the analytes to be measured (i.e., the VOCS) are retained by and concentrated on the adsorbent as the air passes through the tube.

Once the VOCs are collected in this fashion, the tube is then transported to a thermal desorption unit, where the tube is placed in the flow path of an inert gas, such as helium or nitrogen. The tube is subsequently heated, thereby desorbing the analytes, and the carrier gas sweeps the VOCs out of the tube. In some cases, a "trap" is located downstream of the sample tube in order to further pre-concentrate the analytes, and occasionally, remove moisture therefrom, prior to introducing the sample into the chromatographic column. One example is an adsorbent trap, usually cooled to a sub-ambient temperature, which is simply another sorbent tube packed with a suitable adsorbent material, which adsorbs the analytes as the sample gas first passes through the tube, and from which the analytes are then desorbed into the chromatographic column, usually by heating, for subsequent separation and analysis.

Typically, either the column is directly coupled to a sorbent tube in the thermal desorption unit or the unit is connected directly to the column via a transfer line, such as, for example, via a length of fused silica tubing. These arrangements, however, result in a number of disadvantages. One disadvantage is that, in some cases, flow or velocity programming of the carrier gas flowing through the chromatographic column is required, particularly, for example, in applications employing a flow-sensitive detector, such as a mass spectrometer. This control is typically not available from the thermal desorption unit itself. Furthermore, even if it was, the thermal desorption unit would need contemporaneous knowledge of the temperature of the column in order to exercise such control.

Similarly, the supply of carrier gas to the column cannot be interrupted when the column is at an elevated temperature or if an air-sensitive detector, such as a mass spectrometer, is being used. Therefore, if the thermal desorption unit is the only source of carrier gas for the chromatographic column, a complete shutdown of the column and the detector is required any time that maintenance on the thermal desorption unit is necessary, which, in practice, wastes a significant amount of time.

Another problem that exists with these systems is that, in some cases, it is desired to inject liquid samples, either manually or by autosampler, for calibration and diagnostic purposes. However, using the aforementioned system, there is no simple way to accommodate such an injection of liquid from a syringe.

Yet another problem that exists with these systems is that the column connections require significant care to ensure optimal performance, often requiring a skilled operator, which would be required each time a column needs to be installed or replaced.

SUMMARY OF THE INVENTION

The present teachings include systems and methods for communicating analytes from a thermal desorption unit to a chromatographic column that facilitate the control and supply of gas flowing through the column independently of the thermal desorption unit. Further, systems and methods are provided that permit accommodation of syringe injections in chromatographic analyses using thermal desorption units. Also, systems and methods are provided that facilitate connection of chromatographic columns in thermal desorption applications.

To achieve at least some of the objects listed, the invention comprises a chromatographic system for measuring analytes, including a thermal desorption unit for supplying carrier gas containing the analytes to be measured, an interface device in fluid communication with the thermal desorption unit for receiving the analytes therefrom, and a chromatographic column in fluid communication with the interface device for receiving the analytes therefrom, wherein the interface device is adapted to control the fluid flowing into the chromatographic column.

In an embodiment, the invention comprises a method for performing a chromatographic measurement of analytes in a sample, including connecting a thermal desorption unit to an interface device, connecting a chromatographic column to the interface device, supplying fluid containing the analytes from the thermal desorption unit to the interface device, and controlling the fluid flowing into the column with the interface device.

The interface device can control the fluid flowing into the column in several ways, removing the dependence on the thermal desorption unit for this control. In some embodiments, the interface device provides additional carrier gas via a carrier gas inlet to maintain a substantially constant gas flow or velocity. In certain embodiments, the interface device provides a controlled temperature increase via a temperature programmable heating device. In some embodiments, the interface device diverts a portion of the gas received from the thermal desorption unit and vents it from the system via a split vent.

In some embodiments, the interface device is a chromatographic injector. In certain embodiments, both a transfer line from the thermal desorption unit and the column are coupled to the same port. In some embodiments, the distance between the inlet of the column and the port is less than the distance between the outlet of the transfer line and the port, such that the transfer line extends farther up than the column in the interface device.

In certain embodiments, the coupling of both the transfer line and the column to the same port is achieved with an adaptor, which, in some embodiments, includes a first ferrule in which the transfer line is inserted, a second ferrule in which the column is inserted, and a third ferrule coupled to the column port that receives the transfer line and column from the other ferrules and through which the transfer line and column pass up into the interface device. In some of these embodiments, the third ferrule is adapted to be rotated independently of the other ferrules.

In certain embodiments, the interface device includes a septum adapted to receive a syringe for the introduction of liquid samples. In some embodiments, the thermal desorption unit includes a removable sample vessel for obtaining a sample from an environment to be tested, a sample station for receiving the sample vessel positioned in a flow path of carrier gas, and a heating device for heating the vessel to desorb the analytes therein.

DETAILED DESCRIPTION OF THE DRAWINGS

Figure 1:
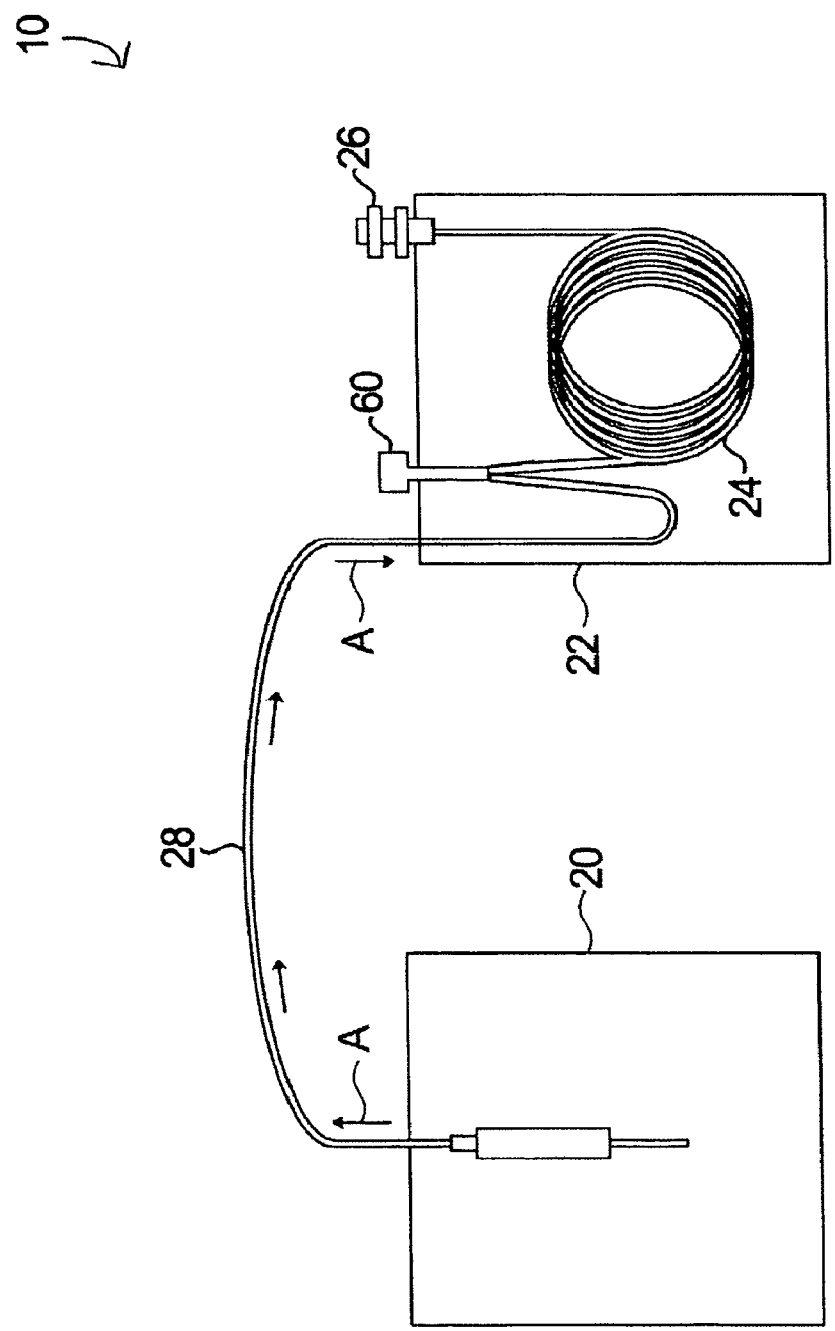
FIG. 1 is a schematic view of a system for interfacing a thermal desorption unit to a chromatographic column in accordance with the invention.

The basic components of one embodiment of a chromatographic system 10 for measuring analytes in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

The system 10 includes a thermal desorption unit 20 and a gas chromatograph 22, which includes a chromatographic column 24 connected to a detector 26. An interface device 60 is mounted to the chromatograph 22, and the column 24 is coupled thereto, such that the column 24 is in fluid communication with the device 60. Similarly, the thermal desorption unit 20 is connected to the interface device 60 via a transfer line 28, through which a sample mixture is communicated to the device 60 (indicated by arrows A), which may, for example, comprise a length of fused silica restrictor tubing.

Figure 2A:
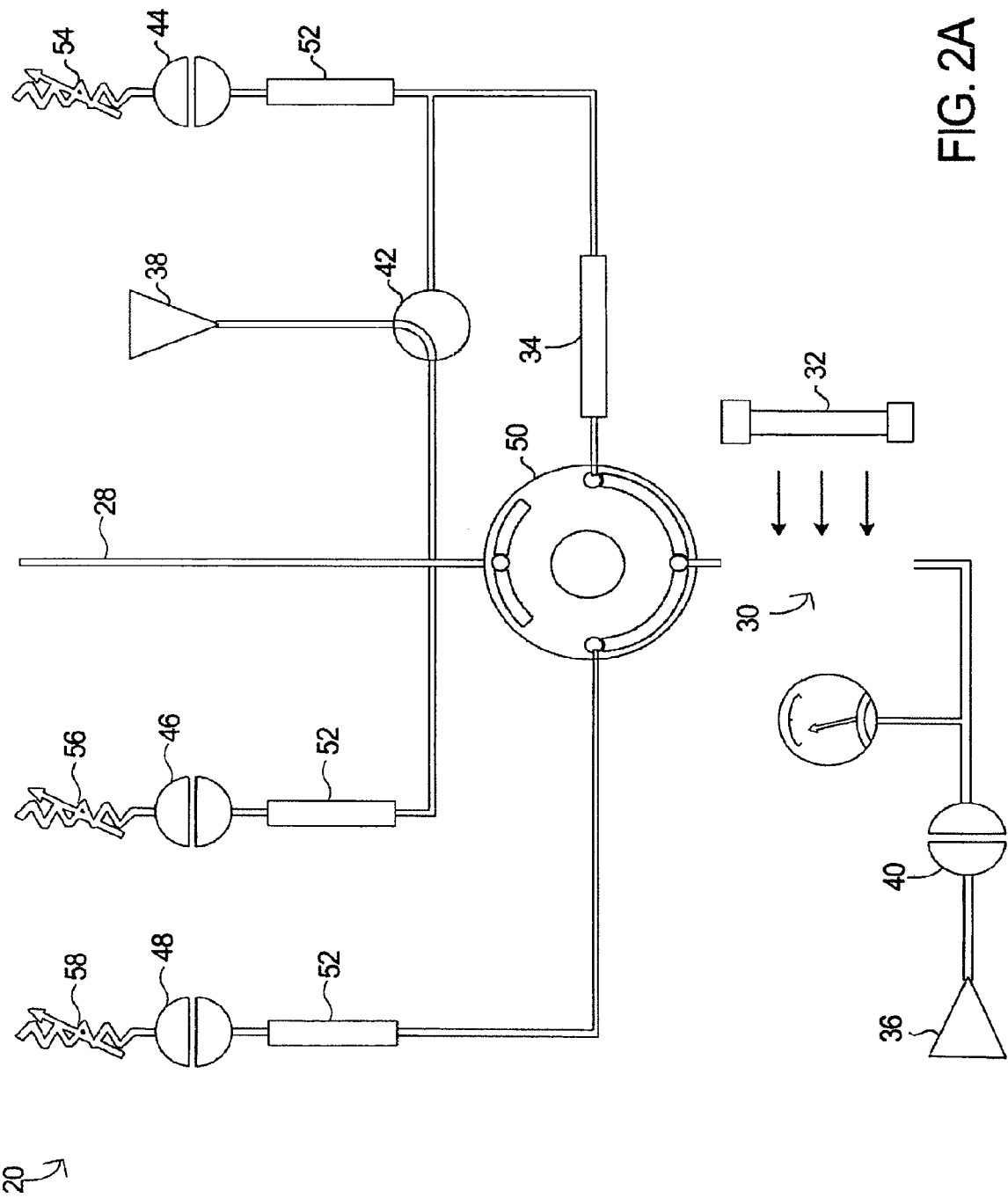
FIG. 2A is a schematic view showing additional detail of the system of FIG. 1.

As illustrated in FIG. 2A, the thermal desorption unit 20 generally comprises a sample station 30, in which a sample vessel 32, such as a sorbent tube, is disposed. In some embodiments, a trap 34, such as another sorbent tube, is placed downstream of the sample tube 32 for further pre-concentration of the analytes. The tube 32, adsorbent trap 34, and transfer line 28 are selectively in communication with each other via a rotary valve 50. A carrier gas inlet 36 is selectively in fluid communication with the sample tube 32 via a valve 40, and another carrier gas inlet 38 is selectively in fluid communication with the adsorbent trap 34 via a valve 42. A desorb vent needle valve 54, an outlet split needle valve 56, and an inlet split needle valve 58 are controlled via solenoid valves 44, 46, 48, respectively, each of which is preceded by a charcoal trap 52.

The interface device 60 can be a device for controlling the temperature of the gas flowing therethrough and/or supplying carrier gas to the gas chromatograph 22. In certain embodiments, the interface device 60 comprises a chromatographic injector, such as, for example, the Programmed-Temperature Split/Splitless Inlet System (PSS) Injector manufactured by PerkinElmer Instruments LLC.

Figure 3:
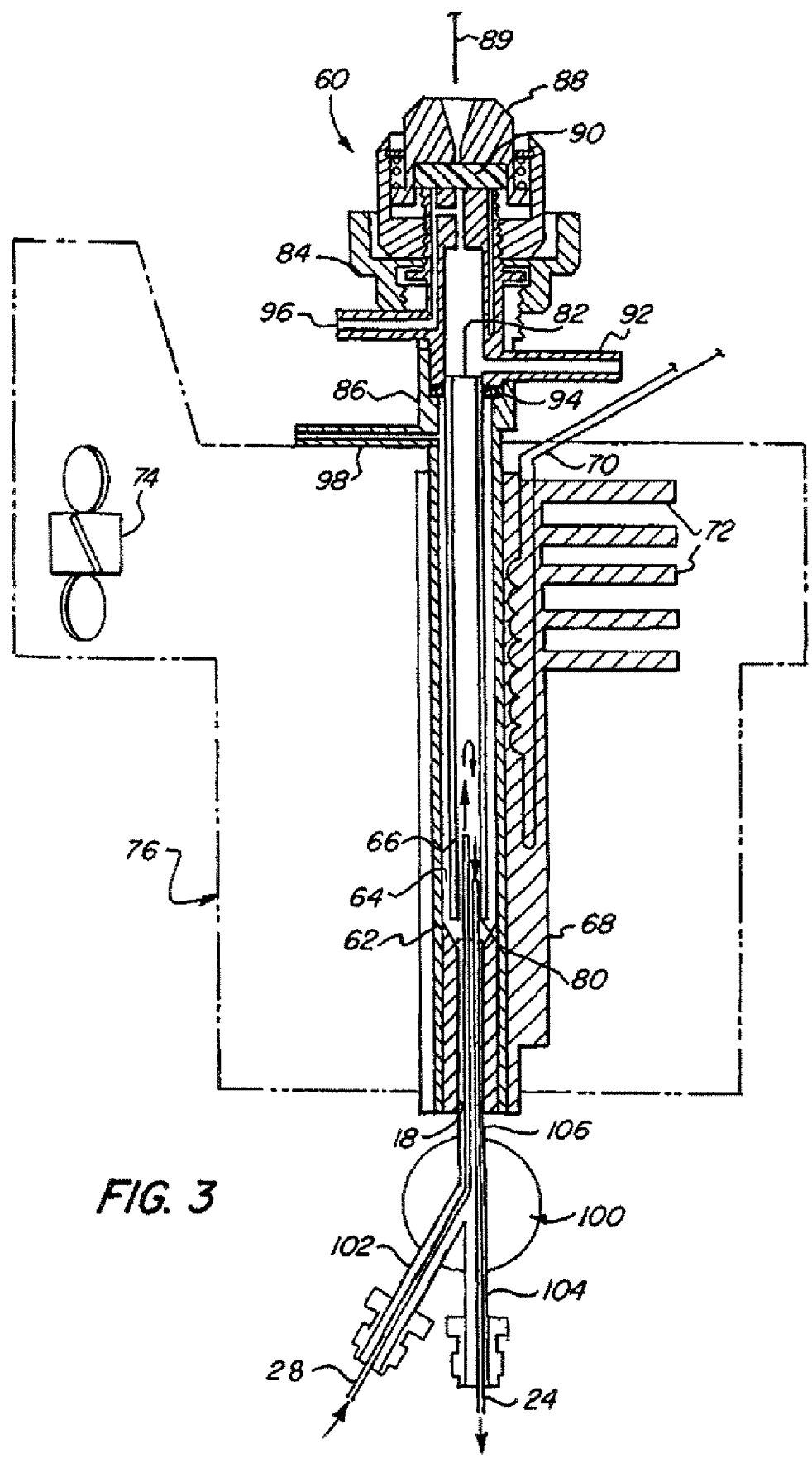
FIG. 3 is a cross-sectional view showing additional detail of the system of FIG. 1.
Figure 4:
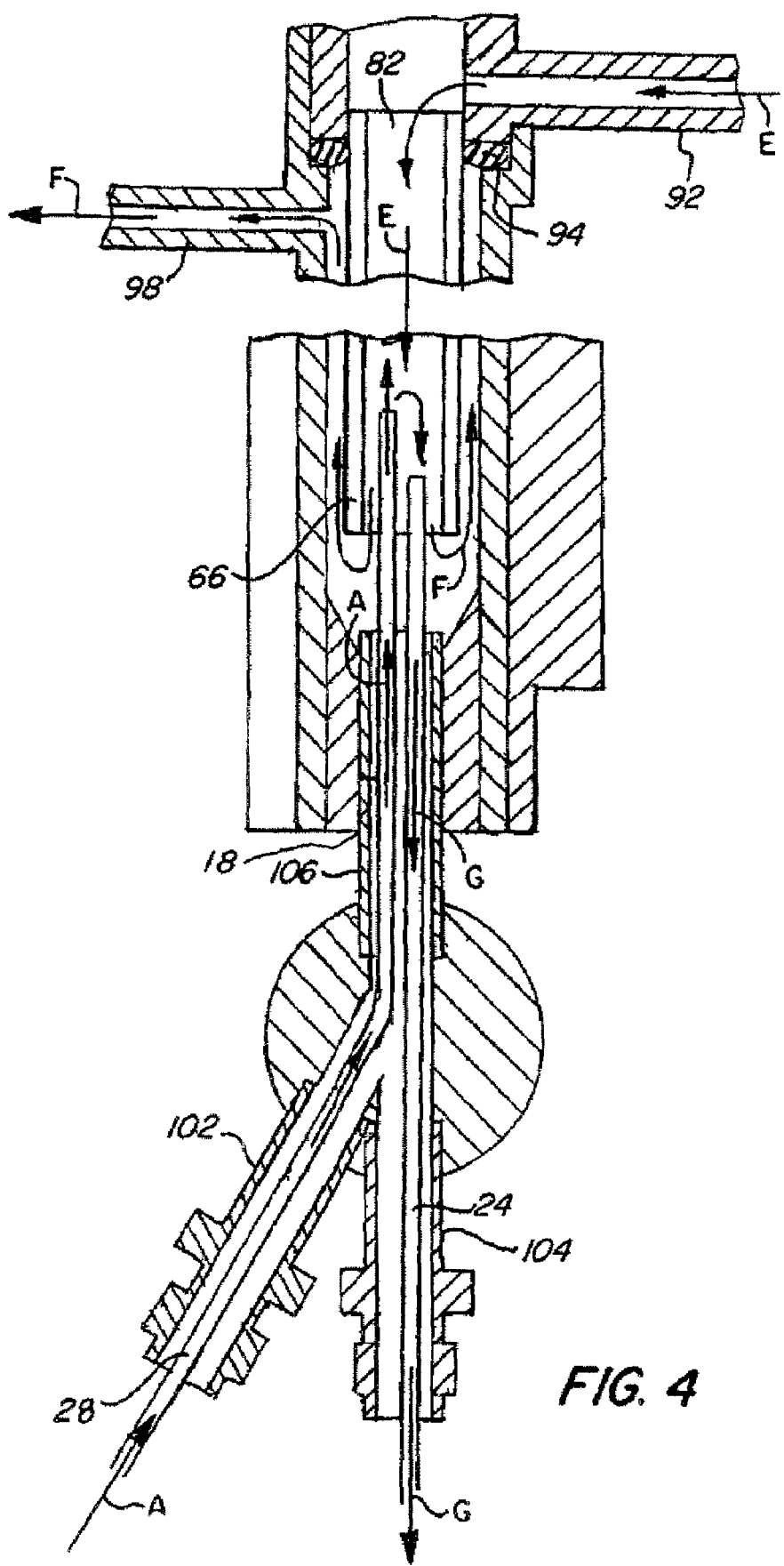
FIG. 4 is a partially cut-away, cross-sectional view showing additional detail of the system of FIG. 1 during the trap desorb stage.

The injector 60 illustrated in FIGS. 3-4 generally includes a metal sleeve 62 that defines a chamber 64, in which a removable tube 66 that serves as the "liner" of the injector 60 is inserted. The sleeve 62 is located inside a heater block 68, which is governed by a heating element 70, for heating the chamber 64, including the liner 66. The heater block 68 is temperature programmable, allowing a controlled increase in temperature, and is provided with cooling fins 72 and a fan 74 coupled to a housing 76 of the injector for subsequently cooling the chamber 64 and liner 66. The liner 66, which is typically a narrow, cylindrical bore tube made of glass, has an inlet 82 located at its top and an outlet 80 located at its bottom. In some embodiments, the outlet 80 is restricted, such that the bottom of the liner 66 has an inner diameter smaller than that of the top, which minimizes any mixing or dispersion of the effluent from the thermal desorption unit 20 with carrier gas inside the injector 60, while allowing a larger top area to account for larger expanding liquid samples.

A threaded collar 84 secures a septum assembly 86 to the housing 76 at the top of the metal sleeve 62. A septum cap 88 secures a septum 90 to the top of the septum assembly 86. Accordingly, a microsyringe 89 can be used to inject a liquid sample through the septum 90, either manually or by autosampler, which may be desired for calibration or diagnostic purposes. As is further explained below, the transfer line 28 itself, like the column 24, is coupled to the bottom of the injector 60 via the column port 18. This ensures that the effluent from the transfer line 28 maintains a high temperature, which is often required in order to keep the large molecules often involved in thermal desorption applications in the vapor phase. Accordingly, the septum 90, which is located at the cooler end of the injector, is typically reserved for the introduction of liquid samples, as noted above.

The illustrated septum assembly 86 has a main carrier gas inlet 92, the pressure of which can be regulated, which is located above, and separated from, the chamber 64 by an internal seal 94, such as an O-ring. Additionally, septum assembly 86 has a septum purge outlet 96. The septum assembly mechanically defines the path of the septum purge flow to prevent cross contamination with the sample flow path.

As noted above, both the transfer line 20 and the column 24 are coupled to the column port 18 to ensure high temperatures. Normally, this would be achieved via a two-hole ferrule. However, several problems usually result from such an arrangement. First, it is often difficult to obtain a good seal with such ferrules. Second, the transfer line and column will be twisted around each other as the ferrule is rotated into the injector, resulting in a high risk of breakage. Even when a good connection is made, it is often difficult to remove either the transfer line or the column alone.

The system 10 employs a special, Y-shaped adaptor 100, which includes ferrules 102, 104, 106. The transfer line 28 is inserted through the ferrule 102, up through the ferrule 106, up into the chamber 64, and into the lower end 80 of the liner 66. Similarly, the column 24 is inserted into the ferrule 104, up through the ferrule 106, up into the chamber 64, and into the lower end 80 of the liner 66. The ferrule 106 can be rotated into the port 18 while holding the rest of the adaptor 100 in place. Accordingly, with this arrangement, the transfer line 28 and column port 24 can each be inserted or removed without affecting the other. The end of the transfer line 28 is offset from, and extends farther up into the liner 66 than, the column 24, thereby facilitating the flow of the sample vapor as further described below.

In certain embodiments, a "split" vent 98, for splitting the gas mixture, is located below the internal seal 94 and is in fluid communication with the chamber 64. Because trap desorption efficiency improves with higher flow rates, the geometry of the transfer line 28 will typically be chosen to provide a desired flow rate for a given pressure drop across it. However, this will typically be more than the flow rate through the column itself, and therefore, excess flow may be diverted to the split vent 98, which results in an attenuation in detector response. By controlling the split vent 98, the operator of the system 10 can find an appropriate compromise trap desorption efficiency (peak shape) and sensitivity (peak size).

Figure 2B:
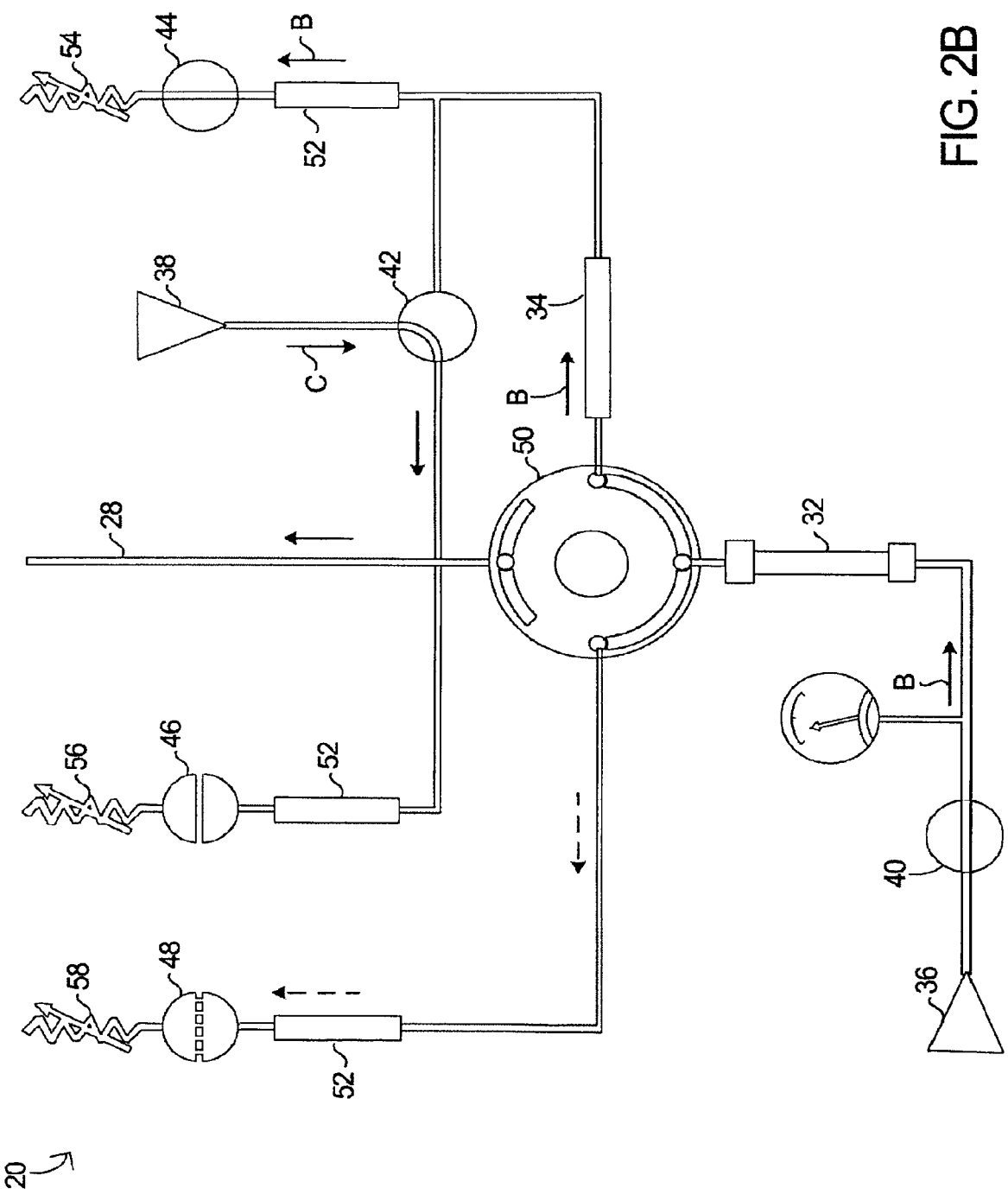
FIG. 2B is a schematic view showing additional detail of the system of FIG. 1 during a tube purge stage.
Figure 2C:
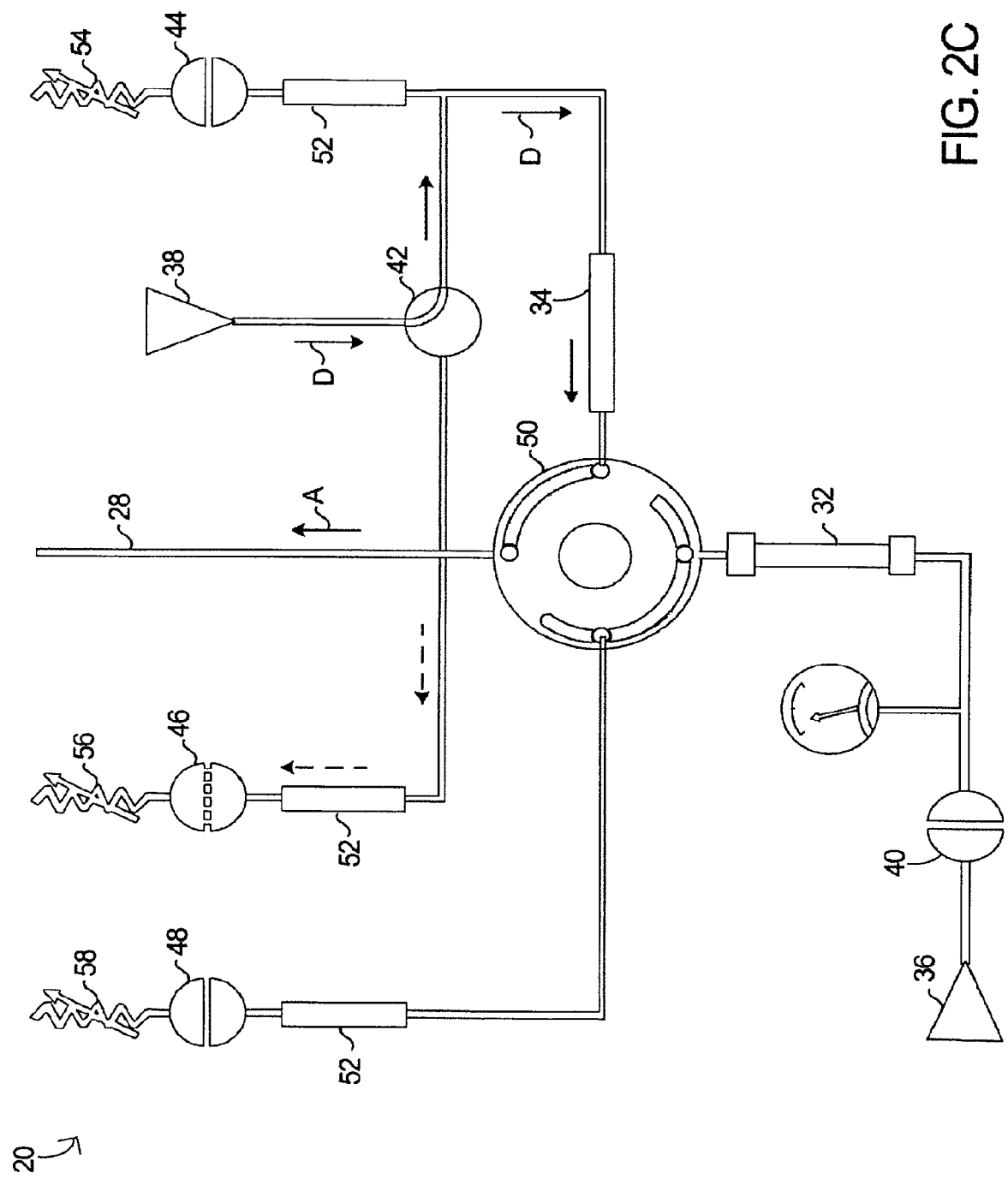
FIG. 2C is a schematic view showing additional detail of the system of FIG. 1 during a trap desorb stage.

The operation of the system 10 is illustrated in FIGS. 1, 2A-C and 4. As shown in FIG. 2A, a sample tube 32, which contains the analytes obtained from the environment to be tested, is disposed in the sample station 30 of the thermal desorption unit 20. As shown in FIG. 2B, with the rotary valve 50 positioned such that the sample tube 32 is in fluid communication with the trap 34, the valves 40, and 44 are opened. The tube 32 is heated in order to desorb the analytes therefrom, and carrier gas flows in through the inlet 36, through the tube 32, and sweeps the analytes into the trap 34. An adsorbent disposed in the trap 34 adsorbs the analytes, and the carrier gas flows out through the valve 54 (indicated by arrows B). Subsequently, as shown in FIG. 2C, the rotary valve 50 is rotated such that the trap 34 is in fluid communication with the transfer line 28, the valves 40 and 44 are closed, and the direction of the valve 42 is switched to place the gas inlet 38 in communication with the trap 34. The trap 34 is heated in order to desorb the analytes therefrom, and carrier gas flows in through the inlet 38 and through the trap 34 (indicated by arrows D), where it sweeps the analytes out of the trap 34 and into the transfer line 28 (indicated by arrows A).

As illustrated in FIGS. 1 and 4, the sample vapor flows along the transfer line 28 until it reaches the injector 60. The injector 60 is maintained at an elevated temperature to ensure that there is no loss of sample or peak distortion due to condensation of the desorbed analytes. The carrier gas inlet 92 of the injector 60 supplies carrier gas, which flows into the liner 66 and down towards the column 24 (indicated by arrows E). In this way, the injector 60 is able to provide a substantially constant flow or velocity of carrier gas through the column 24, regardless of the status of the thermal desorption unit 20. Additionally, the injector 60 may be temperature programmed during the analysis in order to speed up the flow, thereby reducing the time needed for the analysis and reduce any diffusion that may result in peak broadening. The pressure at the inlet of the column 24 will increase as the temperature increases, and thus, the pressure on the thermal desorption unit 20 must be maintained at a higher setting than the injector 60 to ensure a positive flow through the transfer line 28.

The sample vapor flows out through the top of the transfer line 28 into the liner 66 (arrows A), where it encounters the carrier gas flow from the inlet 92 (arrows E), and is directed into the top of the column 24 (indicated by arrows G. As noted above, in certain embodiments, a portion of the flow is diverted out the split vent 98 (indicated by arrows F) in order to obtain an optimal compromise between trap desorption efficiency and sensitivity.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A chromatographic system for measuring analytes, comprising:
    a sampling device for supplying carrier gas containing the analytes to be measured;
    an interface device in fluid communication with said sampling device for receiving the analytes therefrom, said interface device having a column port;
    a transfer line by which the carrier gas containing the analytes is communicated from said sampling device to said interface device, said transfer line having an outlet coupled to said port for communicating the analytes into said interface device;
    a chromatographic column in fluid communication with said interface device, said column having an inlet coupled to said port for receiving the analytes from said interface device; and
    an adaptor by which the outlet of said transfer line and the inlet of said column are coupled to said port;
    wherein said interface device is adapted to control the fluid flowing into said chromatographic column.

2. The system of claim 1, wherein said adaptor comprises:
    a first ferrule into which said transfer line is inserted;
    a second ferrule into which said column is inserted; and
    a third ferrule coupled to said column port that receives said transfer line and said column from said first and second ferrules, and through which said transfer line and said column pass up into said interface device.

3. The system of claim 2, wherein said third ferrule is adapted to be rotated independently of said first and second ferrules.

4. The system of claim 3, wherein said interface device comprises a chromatographic injector.

5. The system of claim 3, wherein the distance between the inlet of said column and said port is less than the distance between the outlet of said transfer line and said port.

6. The system of claim 3, wherein said interface device includes a carrier gas inlet for providing a substantially constant gas flow or velocity into said column.

7. The system of claim 3, wherein said interface device includes a temperature programmable heating device for producing a controlled increase in temperature.

8. The system of claim 3, wherein said interface device includes a split vent for venting a portion of carrier gas received from said sampling device.

9. The system of claim 3, wherein said interface device includes a septum adapted to receive a syringe for introducing fluid samples into said interface device.

10. The system of claim 1, wherein said interface device comprises a chromatographic injector.

11. The system of claim 1, wherein the distance between the inlet of said column and said port is less than the distance between the outlet of said transfer line and said port.

12. The system of claim 1, wherein said interface device includes a carrier gas inlet for providing a substantially constant gas flow or velocity into said column.

13. The system of claim 1, wherein said interface device includes a temperature programmable heating device for producing a controlled increase in temperature.

14. The system of claim 1, wherein said interface device includes a split vent for venting a portion of carrier gas received from said sampling device.

15. A method for performing a chromatographic measurement of analytes in a sample, the method comprising:
   providing an interface device having a column port;
   connecting an adaptor to the column port;
   connecting a sampling device to the adaptor;
   connecting a chromatographic column to the adaptor;
   supplying fluid containing the analytes from the sampling device to the interface device; and
   controlling fluid flowing into the column with the interface device.

16. The method of claim 15, wherein the adaptor comprises:
   a first ferrule into which the transfer line is inserted;
   a second ferrule into which the column is inserted; and
   a third ferrule coupled to the column port that receives the transfer line and the column from the first and second ferrules, and through which the transfer line and the column pass up into the interface device.

17. The method of claim 15, wherein the step of controlling the fluid flowing into the column comprises providing a substantially constant gas flow or velocity to the column via a carrier gas inlet in the interface device.

18. The method of claim 15, wherein the step of controlling the fluid flowing into the column comprises producing a controlled increase in temperature via a temperature programmable heating device in the interface device.

19. The method of claim 15, wherein the step of controlling the fluid flowing into the column comprises venting a portion of carrier gas received from the sampling device through a split vent in the interface device.

20. The method of claim 15, wherein the interface device comprises a chromatographic injector.

* * * * *